(12) United States Patent
Tang

(10) Patent No.: US 7,101,538 B1
(45) Date of Patent: Sep. 5, 2006

(54) POLYESTERAMINE INGREDIENT AND USE OF SAME

(75) Inventor: Diana Tang, Naperville, IL (US)

(73) Assignee: Avon Products, Inc., New York, NY (US)

( * ) Notice: Subject to any disclaimer, the term of this patent is extended or adjusted under 35 U.S.C. 154(b) by 288 days.

(21) Appl. No.: 10/748,597

(22) Filed: Dec. 30, 2003

Related U.S. Application Data

(60) Provisional application No. 60/437,433, filed on Dec. 30, 2002.

(51) Int. Cl.
 *A61K 8/00* (2006.01)

(52) U.S. Cl. .................. 424/70.1; 424/81; 424/401; 424/61; 424/64; 424/47; 424/45; 514/944; 528/288

(58) Field of Classification Search ............. None
See application file for complete search history.

(56) References Cited

U.S. PATENT DOCUMENTS 3,234,156 A * 2/1966 Nimoy et al. ............... 523/457
4,415,728 A * 11/1983 Tremblay ................... 528/279
4,734,523 A * 3/1988 Hofinger et al. ............ 560/196
4,847,416 A * 7/1989 Durvasula et al. .......... 564/443

\* cited by examiner

*Primary Examiner*—Gollamudi S. Kishore
*Assistant Examiner*—Eric E. Silverman
(74) *Attorney, Agent, or Firm*—Ohlandt, Greeley, Ruggiero & Perle, L.L.P.

(57) ABSTRACT

The present invention provides a polyesteramine, a composition having a polyesteramine according to the present invention as an active ingredient and methods for improving hair detangling, wet and dry combing, shine, gloss, conditioning, surface smoothening, water resistance, film-forming properties, static charge reduction and any combination thereof in various personal care products, such as, hair care, skin care, nail care and cosmetic products. Preferably, the polyesteramine is incorporated into a shampoo, hair conditioner, styling mousse, hair treatment preparation, hair coloring product, semi-perm product, oxidation dye, body wash, liquid soap, skin care preparation, lipstick, mascara, color cosmetic, nail care preparation or any combination thereof.

34 Claims, No Drawings

POLYESTERAMINE INGREDIENT AND USE OF SAME

This application claims priority from U.S. Provisional Application Ser. No. 60/437,433, filed Dec. 30, 2002.

BACKGROUND OF THE INVENTION

1. Field of the Invention

The present invention relates to a polyesteramine ingredient and use of the same. More particularly, the present invention relates to the use of the polyesteramine in a variety of personal care, hair care and cosmetic products to provide water resistance, shine, gloss, surface smoothening and film-forming benefits.

2. Description of the Related Art

Water resistance, shine, gloss, surface smoothening, and film-forming are all desirable attributes in personal care, nail care and cosmetic compositions, products and preparations. For example, water resistance is a much-desired quality amongst consumers of color cosmetics, lipsticks, eyelash mascara, insect repellents and sunscreen preparations. Additionally, shine and gloss are much desired attributes in nail color and hair care preparations. Surface smoothening is important in a shampoo, hair conditioner, styling mousse and other hair treatment preparation and can provide superior wet and dry hair combing. Film-forming is a desired attribute in, for example, body wash, liquid soap, hair color and skin care preparations.

There is a long felt need in cosmetic industry for a single ingredient which, when incorporated into formulated compositions, can deliver multiple functions to these compositions, including the aforementioned desired attributes and benefits.

Such results can now be attained by the use of compositions that have an effective amount of a polyesteramine according to the present invention as a single ingredient. This single ingredient delivers multiple performance advantages to a composition that heretofore had required the use of a number of different ingredients. Furthermore, these performance advantages have not been achieved by simple esteramines known in the literature.

SUMMARY OF THE INVENTION

It is an object of the present invention to provide a composition that provides at least one of the following benefits: hair detangling, improved wet and dry combing, shine, gloss, conditioning, surface smoothening, water resistance, film-forming properties, static charge reduction, thickening and surfactant activity.

It is another object of the present invention to provide a composition having a polyesteramine as an active ingredient.

It is still another object of the present invention to provide a personal care product, such as, hair care, skin care, nail care and other cosmetic products, such as, shampoo, hair conditioner, styling mousse, hair treatment preparation, hair coloring product, semi-perm product, oxidation dye, body wash, liquid soap, skin care preparation, lipstick, mascara, color cosmetic, nail care preparation, cream, foam, gel, lotion, solution, pomade, mousse, stick, pump spray, aerosol spray, serum and any combination thereof, which has a polyesteramine.

It is a further object of the present invention to provide a method of applying a composition having a polyesteramine to skin, hair or nail, to produce at least one benefit selected from hair detangling, improved wet and dry combing, shine, gloss, conditioning, surface smoothening, water resistance, film-forming properties, static charge reduction, thickening and surfactant activity.

These and other objects and advantages of the present invention are achieved by the use of a composition having a polyesteramine as an active ingredient in a personal care product, such as, hair care, skin care, nail care and other cosmetic product applications.

DETAILED DESCRIPTION OF THE INVENTION

The present invention relates to a polyesteramine or a polyesteramine compound and its use in a personal care, hair care, nail care or other cosmetic compositions. The unique structure of the polyesteramine according to the present invention allows the polyesteramine to provide multiple benefits, including hair detangling, improved wet and dry combing, shine, gloss, conditioning, surface smoothening, water resistance, film-forming properties, static charge reduction, thickening and/or surfactant activity.

The polyesteramine according to the present invention is represented by the formula:

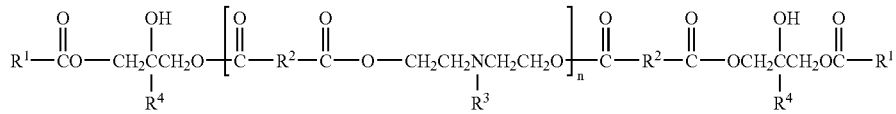

wherein each $R^1$ is independently a linear, branched or cyclic hydrocarbyl group; each $R^2$ is independently the same or different hydrocarbylene group; each $R^3$ is independently hydrogen or a hydrocarbyl group; each $R^4$ is independently hydrogen, methyl or ethyl; and n is an integer from 1 to about 60. More preferably, each $R^1$ in the polyesteramine is independently a linear, branched or cyclic hydrocarbyl group of 3 to 23 carbon atoms, and most preferably each $R^1$ is independently a linear, branched or cyclic hydrocarbyl group of 16 to 22 carbon atoms.

In a preferred embodiment, $R^1$ is a hydrocarbyl group of 17 carbon atoms, which can be the hydrocarbyl group of an isooctadecanoic acid, such as, the hydrocarbyl group of isostearic acid. In another preferred embodiment, $R^1$ is a hydrocarbyl group of 21 carbon atoms, such as, the hydrocarbyl group of behenic acid.

The $R^2$ group in the polyesteramine preferably is a hydrocarbylene group of 1 to 10 carbon atoms. More preferably, $R^2$ is a hydrocarbylene group of 2 to 6 carbon atoms. Thus, when $R^2$ is a hydrocarbylene group of 4 carbon atoms, $R^2$ represents the alkylene group of adipic acid. When $R^2$ is a hydrocarbylene group of 6 carbon atoms, $R^2$ represents the alkylene group of sebacic acid.

The R³ group in the polyesteramine is preferably a hydrocarbyl group of 1 to 6 carbon atoms. Examples of such groups include linear, branched or cyclic hydrocarbyl groups, such as, methyl, ethyl, propyl, butyl, pentyl, hexyl, iso-propyl, iso-butyl, cyclo-propyl, cyclo-butyl, cyclo-pentyl and cyclo-hexyl. Preferably, the R³ group is a hydrocarbyl group of 1 to 3 carbon atoms, and includes methyl, ethyl, propyl, iso-propyl and cyclo-propyl. Most preferably, the R³ group is methyl or ethyl.

The polyesteramine can have any molecular weight that is suitable for a particular application. Generally, however, low molecular weight polyesteramines that have sufficient solubility in the vehicle in a given formulation are preferred. Thus, polyesteramines wherein n is from 1 to 60, generally are suitable for use in a majority of applications. The polyesteramines wherein n is from 1 to 25 are preferred and polyesteramines wherein n is from 1 to 10 are most preferred.

In a preferred embodiment, the polyesteramine is represented by the formula:

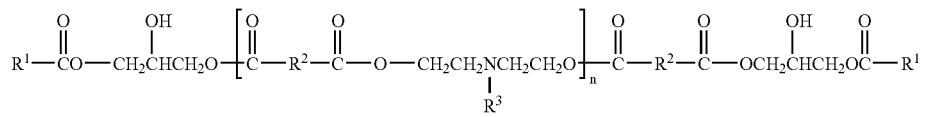

wherein R¹ is a linear, branched or cyclic hydrocarbyl group; R² is a hydrocarbylene group; R³ is selected from the group consisting of: hydrogen and a hydrocarbyl group; and n is an integer from 1 to about 60. More preferably, each R¹ in the polyesteramine is independently a linear, branched or cyclic hydrocarbyl group of 3 to 23 carbon atoms, and most preferably each R¹ is independently a linear, branched or cyclic hydrocarbyl group of 16 to 22 carbon atoms.

The present invention also provides a composition for topical application to hair, skin or nails, which includes a polyesteramine as disclosed herein.

The polyesteramine is present in the composition in an amount effective to provide at least one benefit, such as, hair detangling, improved wet and dry combing, shine, gloss, conditioning, surface smoothening, water resistance, film-forming properties, static charge reduction, thickening or surfactant activity.

Preferably, the composition is in a form, such as, shampoo, hair conditioner, styling mousse, hair treatment preparation, hair coloring product, semi-perm product, oxidation dye, body wash, liquid soap, skin care preparation, lipstick, mascara, color cosmetic, nail care preparation (e.g., enamel) or any combination thereof.

Preferably, the polyesteramine is present in the composition in an amount from about 0.01 wt % (weight percent) to about 40 wt % based on the total weight of the composition. More preferably, the polyesteramine is present in an amount from about 0.05 wt % to about 20 wt % based on the total weight of said composition. Most preferably, the polyesteramine is present in an amount from about 0.1 wt % to about 10 wt % based on the total weight of the composition.

The composition can further include one or more additional components selected from antimicrobials, antioxidants, buffering agents, chelating agents, colorants, conditioning agents, emollients, emulsifiers, film formers, fragrances, humectants, lubricants, moisturizers, pigments, preservatives, skin penetration enhancers, stabilizers, surfactants, thickeners, viscosity modifiers, vitamins or any combination thereof.

When the composition is a hair conditioner, the polyesteramine is present in an amount from about 0.01 wt % to about 10 wt % based on the total weight of said composition, and preferably from about 0.1 wt % to about 5 wt % based on the total weight of the composition.

When the composition is a hair styling product, the polyesteramine is present in an amount from about 0.1 wt % to about 10 wt % based on the total weight of the composition.

When the composition is a styling gel, the polyesteramine is present in an amount from about 0.1 wt % to about 4.0 wt % based on the total weight of the composition.

When the composition is a body wash, the polyesteramine is present in an amount from about 0.1 wt % to about 4 wt % based on the total weight of the composition.

When in the form of a shampoo, the hair care compositions of the present invention typically have one or more surfactants present in an amount sufficient to clean the hair. Preferably, the amount is about 5 wt % to about 20 wt % based on the total weight of the composition. The surfactants in shampoo compositions can include anionic, nonionic or amphoteric surfactants, or mixtures of these surfactants.

When in the form of a leave-on conditioner, the compositions of the present invention preferably have a relatively smaller amount of a non-ionic surfactant typically in the range from about 0.01 wt % to about 3.0 wt % based on the total weight of the composition. When in the form of a leave-on conditioner, the compositions preferably have a fatty alcohol and an ethoxylated fatty alcohol having from about 12 to about 36 carbon atoms. Such fatty alcohols and ethoxylated alcohols are typically present in an amount from about 0.01 wt % to about 5.0 wt % based on the total weight of the composition. Examples of such fatty alcohols include, but are not limited to, lauryl alcohol, cetyl alcohol, stearyl alcohol, behenyl alcohol, or any combinations thereof. Examples of such ethoxylated fatty alcohols include all fatty alcohols with the ethoxylation from 2 moles to 30 moles.

The present compositions typically have a vehicle. The vehicle should be a physiologically acceptable or suitable vehicle. In the context of the present invention, the term "physiologically acceptable vehicle" or "suitable vehicle" refer to any vehicle for a drug, a cosmetic or a medicament that is suitable for use in direct, safe contact with human tissues.

Preferably, the polyesteramine is incorporated into a suitable topical vehicle to form a topical formulation prior to applying.

The compositions having the polyesteramine of the present invention can be in a number of different product forms. Such suitable product forms include a cream, aerosol or pump spray, mousse, foam, gel, lotion, stick, pomade, solution, or a product form in which the polyesteramine is incorporated into a patch or towelette.

The polyesteramine according to the present invention can be prepared by methods known to those skilled in the art, for example, by contacting the components of a reaction mixture, which includes:

(a) a diethanolamine compound represented by the formula:

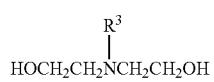

(b) a dicarboxylic acid represented by the formula:

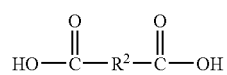

(c) a triol represented by the formula:

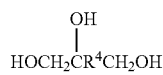

and (d) a monocarboxylic acid represented by the formula:

wherein each $R^1$ is independently a linear, branched or cyclic hydrocarbyl group of 16–22 carbon atoms; each $R^2$ is independently a hydrocarbylene group; each $R^3$ is independently hydrogen or a hydrocarbyl group; and each $R^4$ is independently hydrogen, methyl or ethyl.

The contacting step is carried out under conditions sufficient to produce a polyesteramine according to the present invention, wherein n is an integer from 1 to about 60.

The components of the reaction mixture can be contacted either sequentially or simultaneously. Preferably, the diethanolamine compound, said dicarboxylic acid, said triol and said monocarboxylic acid are contacted in a molar ratio of 1.4–1.6 moles of said dicarboxylic acid, 1.4–1.6 moles of said triol and 1.4–1.6 moles of said monocarboxylic acid to each mole of said diethanolamine compound. Preferably, the contacting is carried out in the presence of an esterification catalyst, such as, a protic, organometallic or Lewis acid catalyst.

The present invention further includes methods of using the composition according to the present invention that have a polyesteramine as an active ingredient in various personal care products, such as, hair care, skin care, nail care and cosmetic products.

In one aspect, the present invention provides a method of imparting to hair, skin or nails an attribute selected from hair detangling, improved wet and dry combing, shine, gloss, conditioning, surface smoothening, water resistance, film-forming properties, static charge reduction or any combination thereof.

The method includes the step of applying onto the hair, skin or nails an effective amount of a composition having a polyesteramine according to the present invention.

In another aspect, the present invention provides a method of enhancing the appearance of hair. The method includes the steps of applying onto the hair an effective amount of a composition having a polyesteramine according to the present invention.

In still another aspect, the present invention provides a method of styling hair to produce improved styling hold and/or improved curl retention. The method includes the step of applying onto the hair an effective amount of a composition having a polyesteramine according to the present invention.

In yet another aspect, the present invention provides a method of conditioning hair. The method includes the step of applying onto the hair an effective amount of a composition having a polyesteramine according to the present invention. Hair treated in this manner has improved smoothness.

In a further aspect, the present invention provides a method of cleansing skin. The method includes the step of applying onto the skin an effective amount of the composition having a polyesteramine according to the present invention.

The invention is further described in the following example, which is intended to be illustrative and not limiting.

Wet Comb Method

The performance of the polyesteramine material in a conditioner base was compared with stearamidopropyl dimethylamine, a conditioning agent that is commonly used to serve as the standard for the comparison. Representative formulas are shown in the Table herein below:

TABLE

Conditioner Composition A Having Polyesteramine and
Conditioner Composition B Having Stearamidopropyl Dimethylamine

|  | A | B |
|---|---|---|
| water | 94.4 | 94.4 |
| ethyl hydroxyethylcellulose | 1.0 | 1.0 |
| ceteareth-20 | 0.5 | 0.5 |
| cetyl alcohol | 1.0 | 1.0 |
| stearyl alcohol | 2.5 | 2.5 |
| polyesteramine | 0.5 | — |
| stearamidopropyl dimethylamine | — | 0.5 |
| Kathon CG[a] | 0.1 | 0.1 |

[a]Kathon CG is a mixture of methylchloroisothiazolinone and methylisothiazolinone, available commercially from Rohm & Haas Co., Philadelphia, PA.

To evaluate the utility of the polyesteramine as a detangling agent for improved combing, wet comb tensile studies were performed using a Dia-Stron MTT170 Miniature Tensile Testing Unit and corresponding software MTTW in Version 6.0, available from Diastron Limited. Hair swatches used for studies were one by six inch, medium density, Caucasian brown tresses purchased from International Hair Importers and Products, Inc., Floral Park, N.Y. For each test run 0.5 mL of product was applied to the hair tress. Wet comb tensile studies resulted in total work reduction of 20.63% for formula A, while formula B had a total work reduction of 18.11%. Total work is defined herein as the amount of force required to comb through the hair tress. Thus, the polyesteramine material does indeed provide significant conditioning benefits that are greater than benefits provided by conditioners commonly used in the industry.

The following are examples of compositions having the polyesteramine according to the present invention.

| Ingredient | Weight % |
|---|---|
| Shampoo | |
| Distilled water | QS |
| Guar Hydroxypropyltromonium Chloride | 0.4 |
| Citric acid | 0.1 |
| Disodium EDTA | 0.1 |
| Methylparaben | 0.2 |
| Cocamide MEA | 2.0 |
| Glycol Distearate | 0.75 |
| Na Lauryl Ether Sulfate | 18.0 |
| Polyesteramine | 1.0 |
| Fragrance | 0.5 |
| Methylisothiazolinone, Methylchloroisothiazolinone | 0.066 |
| Conditioner | |
| Distilled water | QS |
| HEC and Dialkyldimethyl Ammonium Chloride | 0.25 |
| Polyesteramine | 2.0 |
| Citric acid | 0.3 |
| Disodium EDTA | 0.1 |
| Methylparaben | 0.2 |
| Cetearyl alcohol/Cetearth-20 | 0.3 |
| Stearamidopropyl Dimethylamine | 0.5 |
| Cetyl Alcohol | 2.0 |
| Cetyl/stearyl Alcohol | 4.0 |
| Propylparaben | 0.1 |
| Phenoxyethanol | 0.5 |
| Fragrance | 0.75 |
| Mousse | |
| Distilled water | QS |
| Imidazolidinyl Urea | 0.5 |
| HEC and Dialkyldimethyl Ammonium Chloride | 3.0 |
| Polyesteramine | 1.0 |
| Isoceteth-20 | 0.5 |
| Fragrance | 0.3 |
| Gel | |
| Distilled water | 91.6 |
| Disodium EDTA | 0.1 |
| Imidazolidinyl Urea | 0.5 |
| Carbomer | 0.5 |
| Aminomethyl Propanol | 0.5 |
| PVPVA copolymer | 6.0 |
| Polyesteramine | 0.5 |
| Fragrance | 0.3 |
| Body Wash | |
| Polyesteramine | 1.0 |
| Fatty acids (e.g., Lauric acid, Myristic acid, Palmitic acid, Stearic acid) | 20.5 |
| Glycerin | 5.0 |
| Potassium hydroxide | 5.0 |
| Sodium chloride | 2.7 |
| Sodium auroamphoacetate | 2.5 |
| Propylene glycol | 1.5 |
| Glycol distearate | 1.25 |
| Fragrance | 1.0 |
| PEG-6 | 0.5 |
| Triclosan | 0.3 |
| Imidazolidinyl urea | 0.2 |
| Tetrasodium EDTA | 0.05 |
| Distilled water | QS |
| Lipstick | |
| Polyesteramine | 0.5 |
| Fatty acid esters (e.g., Octyl palmitate, Isopropyl palmitate, Cetyl lactate, Caprylic/Capric triglyceride | 22.5 |

-continued

| Ingredient | Weight % |
|---|---|
| Wax (e.g., Beeswax, Candellila, Ozokerite, Carnuba) | 18.0 |
| Octyl dimethyl PABA | 3.0 |
| Lecithin | 0.3 |
| Allantoin | 0.2 |
| Preservatives (e.g., BHT,BHA) | 0.02 |
| Pigments (e.g., D&C Red No. 6 Barium Lake, D&C Red No. 27 Aluminum Lake, D&C Red No. 21 Aluminum Lake, D&C Red No. 7 Calcium Lake) | 11.0 |
| Titanium dioxide | 1.0 |
| Oil (e.g., Castor oil, Sesame oil, Soybean oil, Hydrogenated soybean oil, Lanolin oil) | QS |
| Mascara | |
| Polyesteramine | 0.3 |
| Pentaerythrityl tetrastearate | 9.0 |
| Waxes (e.g., Beeswax, Ozokerite, Candelilla, Carnuba) | 12.5 |
| Glyceryl stearate | 4.7 |
| PVP/Eicosene | 4.25 |
| Oleic acid | 2.8 |
| Polyisobutane | 2.6 |
| Ammonium acrylates copolymer | 1.95 |
| Triethanolamine | 1.7 |
| Sorbitan sesquioleate | 1.0 |
| Benzyl alcohol | 0.8 |
| Vitamins (e.g., Panthenol, Tocopheryl acetate calcium pantothenate) | 0.5 |
| Sodium silicoaluminate | 0.5 |
| Sodium hexametaphosphate | 0.4 |
| Preservatives (e.g., Methylparaben, Propylparaben) | 0.6 |
| Propylene glycol | 0.25 |
| AMP-Isostearic hydrolyzed keratin | 0.1 |
| Sodium lauryl sulfate | 0.05 |
| SD alcohol 40 | 0.02 |
| Potassium sorbate | 0.02 |
| Propylene glycol stearate | 0.01 |
| EDTA | 0.005 |
| Pigments (e.g., Ultramarines, Carmine) | 14 |
| Distilled water | QS |

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

What is claimed is:

1. A composition for topical application to hair, skin or nails, comprising:

a polyesteramine compound represented by the formula:

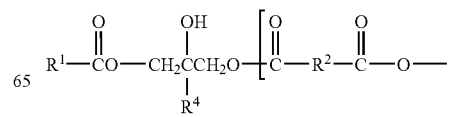

-continued

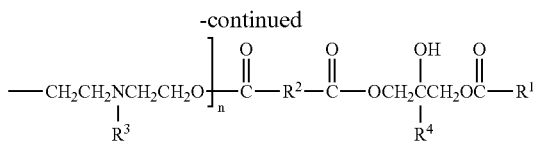

wherein each $R^1$ is independently selected from the group consisting of: a linear, branched or cyclic hydrocarbyl group; each $R^2$ is independently the same or different hydrocarbylene group; each $R^3$ is independently selected from the group consisting of: hydrogen and a hydrocarbyl group; each $R^4$ is independently selected from the group consisting of: hydrogen, methyl and ethyl; and n is an integer from 1 to about 60.

2. The polyesteramine of claim 1, wherein $R^1$ is a hydrocarbyl group of 3 to 23 carbon atoms.

3. The polyesteramine of claim 1, wherein $R^1$ is a hydrocarbyl group of 16 to 22 carbon atoms.

4. The composition of claim 1, wherein $R^1$ is a hydrocarbyl group of 17 carbon atoms, which is the hydrocarbyl group of isooctadecanoic acid.

5. The composition of claim 1, wherein $R^1$ is a hydrocarbyl group of 17 carbon atoms, which is the hydrocarbyl group of isostearic acid.

6. The composition of claim 1, wherein $R^1$ is a hydrocarbyl group of 21 carbon atoms, which is the hydrocarbyl group of behenic acid.

7. The composition of claim 1, wherein $R^2$ is a hydrocarbylene group of 1 to 10 carbon atoms.

8. The composition of claim 1, wherein $R^2$ is a hydrocarbylene group of 2 to 6 carbon atoms.

9. The composition of claim 1, wherein $R^2$ is the alkylene group of adipic acid.

10. The composition of claim 1, wherein $R^3$ is a hydrocarbyl group of 1 to 6 carbon atoms.

11. The composition of claim 10, wherein $R^3$ is a hydrocarbyl group of 1 to 3 carbon atoms.

12. The composition of claim 11, wherein $R^3$ is a methyl.

13. The composition of claim 1, wherein n is an integer from 1 to 25.

14. The composition of claim 13, wherein n is an integer from 1 to 10.

15. The composition of claim 1, wherein said polyesteramine is represented by the formula:

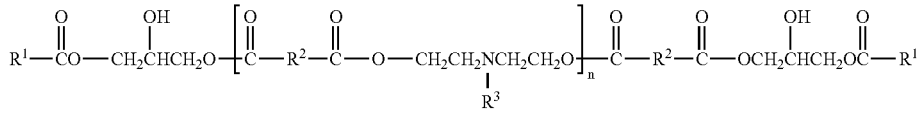

wherein $R^1$ is a linear, branched or cyclic hydrocarbyl group of 16 to 22 carbon atoms; $R^2$ is a hydrocarbylene group; $R^3$ is selected from the group consisting of: hydrogen and a hydrocarbyl group; and n is an integer from 1 to about 60.

16. The composition of claim 1, wherein said polyesteramine is present in said composition in an amount effective to provide at least one benefit selected from the group consisting of: hair detangling, improved wet and dry combing, shine, gloss, conditioning, surface smoothening, water resistance, film-forming properties, static charge reduction, thickening and surfactant activity.

17. The composition of claim 1, wherein said composition is in a form selected from the group consisting of: shampoo, hair conditioner, styling mousse, hair treatment preparation, hair coloring product, semi-perm product, oxidation dye, body wash, liquid soap, skin care preparation, lipstick, mascara, color cosmetic, nail care preparation, cream, foam, gel, lotion, solution, pomade, mousse, stick, pump spray, aerosol spray and any combination thereof.

18. The composition of claim 1, wherein said polyesteramine is present in an amount from about 0.01 wt % to about 40 wt % based on the total weight of the composition.

19. The composition of claim 18, wherein said polyesteramine is present in an amount from about 0.05 wt % to about 20 wt % based on the total weight of the composition.

20. The composition of claim 19, wherein said polyesteramine is present in an amount from about 0.1 wt % to about 10 wt % based on the total weight of the composition.

21. The composition of claim 1, further comprising one or more additional components selected from the group consisting of: antimicrobials, antioxidants, buffering agents, chelating agents, colorants, conditioning agents, emollients, emulsifiers, film formers, fragrances, humectants, lubricants, moisturizers, pigments, preservatives, skin penetration enhancers, stabilizers, surfactants, thickeners, viscosity modifiers, vitamins and any combination thereof.

22. The composition of claim 1, wherein the composition is a hair conditioner and wherein said polyesteramine is present in an amount from about 0.01 wt % to about 10 wt % based on the total weight of the composition.

23. The composition of claim 1, wherein the polyesteramine is present in an amount from about 0.1 wt % to about 5 wt % based on the total weight of the composition.

24. The composition of claim 1, wherein the composition is a hair styling product and wherein said polyesteramine is present in an amount from about 0.1 wt % to about 10 wt % based on the total weight of the composition.

25. The composition of claim 1, wherein the composition is a styling gel and wherein said polyesteramine is present in an amount from about 0.1 wt % to about 4.0 wt % based on the total weight of the composition.

26. The composition of claim 1, wherein the composition is a body wash wherein said polyesteramine is present in an amount from about 0.1 wt % to about 4 wt % based on the total weight of the composition.

27. A method of imparting to hair, skin or nails an attribute selected from the group consisting of: hair detangling, improved wet and dry combing, shine, gloss, conditioning, surface smoothening, water resistance, film-forming properties, static charge reduction and any combination thereof, said method comprising:
applying onto said hair, skin or nails an effective amount of the composition of claim 1.

28. The method of claim 27, wherein said composition is in a form selected from the group consisting of: shampoo, hair conditioner, styling mousse, hair treatment preparation, hair coloring product, semi-perm product, oxidation dye, body wash, liquid soap, skin care preparation, lipstick, mascara, color cosmetic, nail care preparation, cream, foam, gel, lotion, solution, pomade, mousse, stick, pump spray, aerosol spray and any combination thereof.

29. The method of claim 27, wherein said polyesteramine is present in an amount from about 0.1 wt % to about 10 wt % based on the total weight of the composition.

30. A method of enhancing the appearance of hair comprising:

applying onto said hair an effective amount of the composition of claim 1.

31. A method of styling hair to produce improved styling hold and/or improved curl retention, said method comprising:

applying onto said hair an effective amount of the composition of claim 1.

32. A method of conditioning hair comprising:

applying onto said hair an effective amount of the composition of claim 1.

33. The method of claim 32, wherein said hair has improved smoothness.

34. A method of cleansing skin comprising:

applying to said skin an effective amount of the composition of claim 1.

* * * * *